US011690660B2

(12) United States Patent
Hartson et al.

(10) Patent No.: US 11,690,660 B2
(45) Date of Patent: Jul. 4, 2023

(54) GUIDES, INSTRUMENTS, SYSTEMS AND METHODS OF USE

(71) Applicant: Paragon 28, Inc., Englewood, CO (US)

(72) Inventors: Kyle James Hartson, Denver, CO (US); Randy Allard, Golden, CO (US); Albert Dacosta, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 795 days.

(21) Appl. No.: 16/508,955

(22) Filed: Jul. 11, 2019

(65) Prior Publication Data

US 2020/0015874 A1 Jan. 16, 2020

Related U.S. Application Data

(63) Continuation of application No. PCT/US2019/041146, filed on Jul. 10, 2019.

(60) Provisional application No. 62/695,838, filed on Jul. 10, 2018.

(51) Int. Cl.
| | | |
|---|---|---|
| *A61B 17/70* | (2006.01) | |
| *A61B 17/88* | (2006.01) | |
| *A61B 17/66* | (2006.01) | |
| *A61B 90/70* | (2016.01) | |
| *A61B 17/90* | (2006.01) | |

(52) U.S. Cl.
CPC ......... *A61B 17/8897* (2013.01); *A61B 17/66* (2013.01); *A61B 90/70* (2016.02); *A61B 17/90* (2021.08); *A61B 2560/04* (2013.01)

(58) Field of Classification Search
CPC ..... A61B 17/8897; A61B 17/66; A61B 17/90; A61B 17/1775; A61B 17/1682; A61B 17/32; A61B 17/15; A61B 17/17; A61B 17/88; A61B 17/1796; A61B 90/70; A61B 2560/04
USPC ..... 606/53, 79, 80, 84, 85, 87, 96, 102, 104
See application file for complete search history.

(56) References Cited

U.S. PATENT DOCUMENTS

| | | | | |
|---|---|---|---|---|
| 4,704,760 A | * | 11/1987 | Grieshaber | ............ A61B 90/70 |
| | | | | 15/218.1 |
| 5,246,444 A | * | 9/1993 | Schreiber | ............... A61B 17/15 |
| | | | | 606/87 |
| 6,165,177 A | | 12/2000 | Wilson et al. | |
| 7,959,635 B1 | | 6/2011 | Bonutti | |

(Continued)

FOREIGN PATENT DOCUMENTS

WO 2017011656 1/2017

OTHER PUBLICATIONS

International Search Report and Written Opinion of the International Searching Authority for PCT/US2019/041146, dated Sep. 24, 2019, 10 pages.

(Continued)

*Primary Examiner* — Eduardo C Robert
*Assistant Examiner* — David C Comstock
(74) *Attorney, Agent, or Firm* — Heslin Rothenberg Farley & Mesiti P.C.; Jacquelyn A. Graff, Esq.

(57) ABSTRACT

Guides, instruments, devices, systems and methods for maintaining, correcting and/or resurfacing the multiple bones of a joint are disclosed. The guide system includes a cut guide and an alignment guide for engagement with the cut guide. The guide system also includes a cleaning system with a guide and a cutting instrument. Methods of using the guide system and cleaning system are also disclosed.

18 Claims, 17 Drawing Sheets

(56) References Cited

U.S. PATENT DOCUMENTS

| | | | |
|---|---|---|---|
| 2003/0196289 A1* | 10/2003 | Schwab | B08B 1/00 15/210.1 |
| 2005/0075641 A1 | 4/2005 | Singhatat | |
| 2006/0058809 A1 | 3/2006 | Zink et al. | |
| 2008/0262500 A1 | 10/2008 | Collazo | |
| 2009/0270864 A1 | 10/2009 | Poncet | |
| 2014/0081275 A1* | 3/2014 | Metzger | A61B 17/1764 606/88 |
| 2015/0134011 A1* | 5/2015 | Medoff | A61B 17/1728 606/286 |
| 2015/0257899 A1* | 9/2015 | Luna | A61B 17/1739 623/21.18 |
| 2015/0305752 A1* | 10/2015 | Eash | A61B 17/157 606/88 |
| 2016/0199076 A1* | 7/2016 | Fallin | A61B 17/1739 606/301 |
| 2016/0213384 A1 | 7/2016 | Fallin et al. | |
| 2016/0235414 A1* | 8/2016 | Hatch | A61B 17/151 |
| 2017/0014143 A1* | 1/2017 | Dayton | A61B 17/8061 |
| 2017/0079669 A1* | 3/2017 | Bays | A61B 17/1739 |
| 2019/0099189 A1* | 4/2019 | Fallin | A61B 17/151 |
| 2019/0336140 A1* | 11/2019 | Dacosta | A61B 17/15 |
| 2020/0046412 A1* | 2/2020 | Nachtrab | A61B 17/17 |
| 2020/0060690 A1* | 2/2020 | Woodard | A61B 17/15 |

OTHER PUBLICATIONS

Partial Supplementary European Search Report issued in European Patent Application No. 19833523.4, dated Mar. 14, 2022, 12 pages.

\* cited by examiner

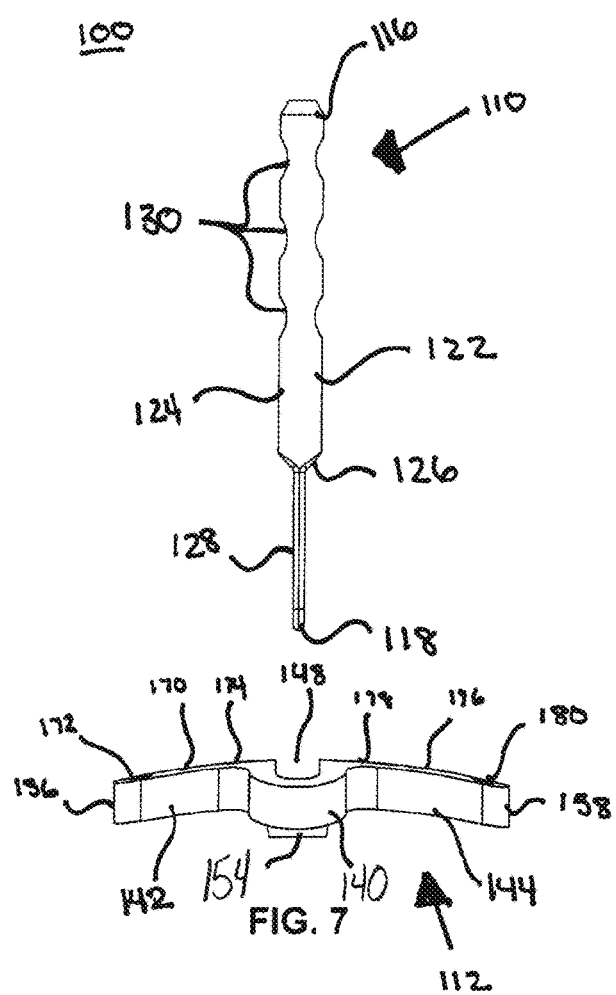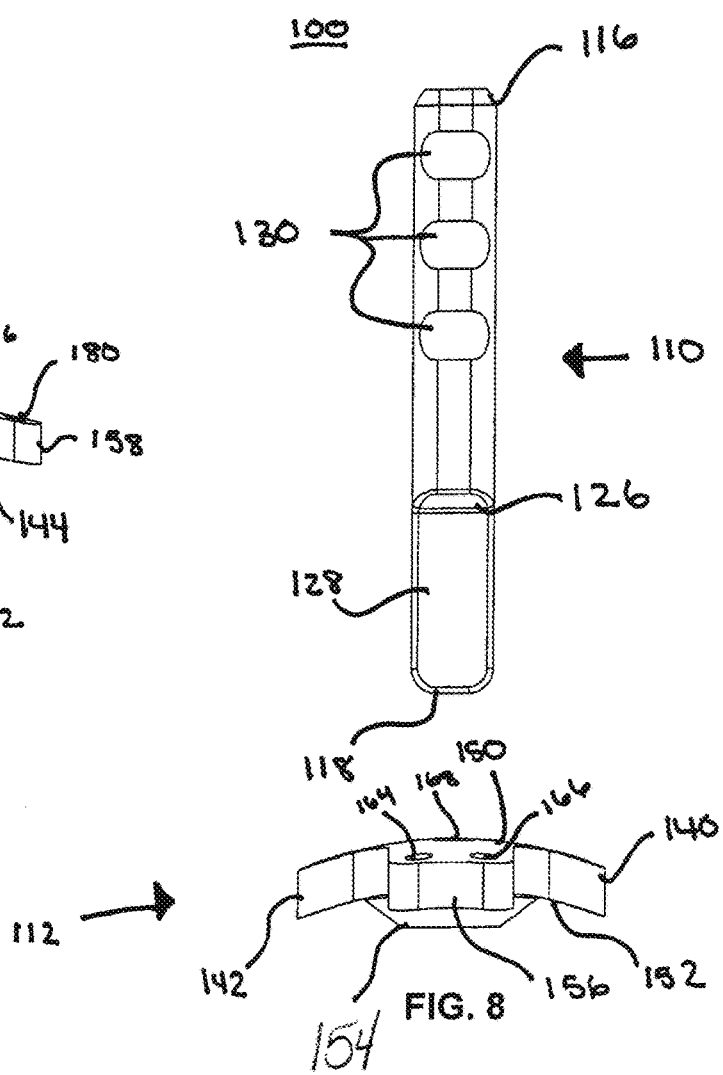
FIG. 7
FIG. 8

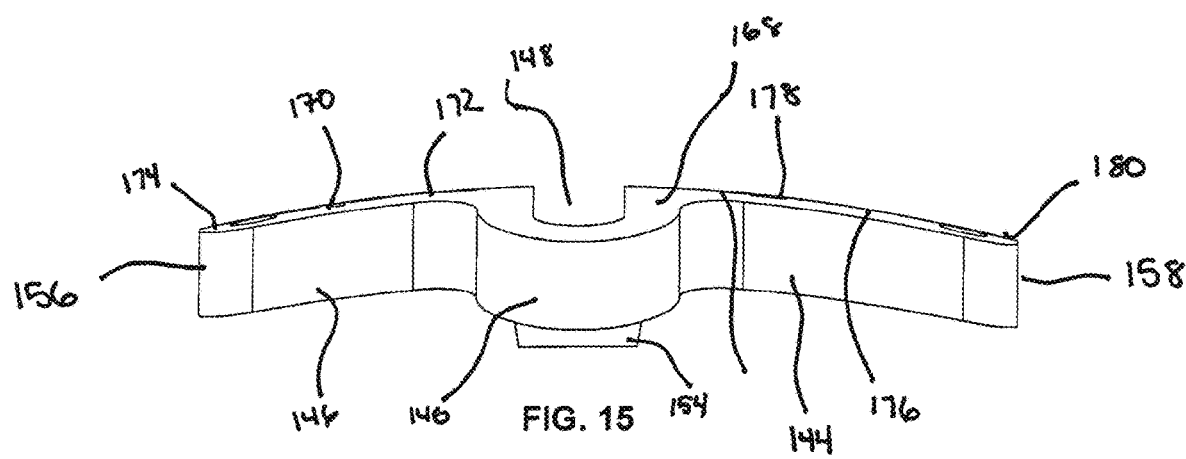
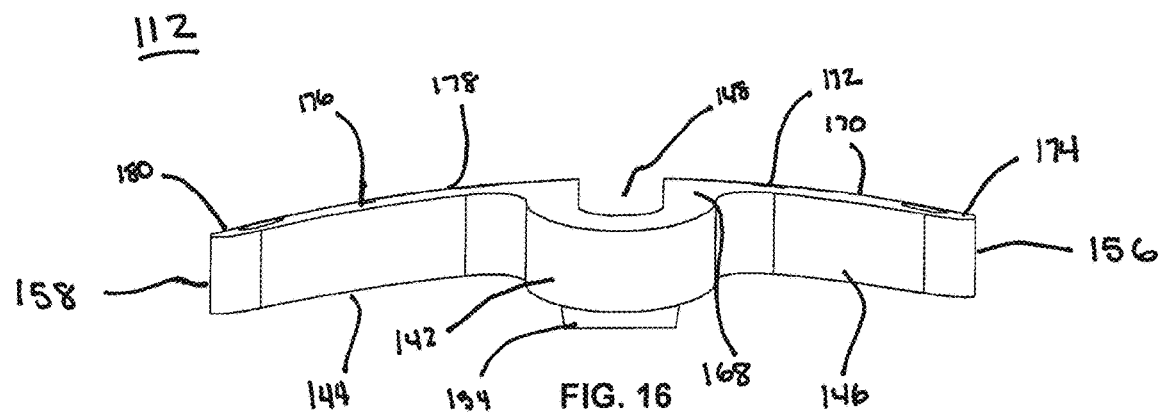

300

300

GUIDES, INSTRUMENTS, SYSTEMS AND METHODS OF USE

CROSS REFERENCE TO RELATED APPLICATION

This application is a continuation of PCT Application No. PCT/US2019/041146 filed on Jul. 10, 2019, entitled Guides, Instruments, Systems and Methods of Use, which claims priority benefit under 35 U.S.C. § 119(e) of U.S. provisional application No. 62/695,838 filed Jul. 10, 2018, entitled Guides, Instruments, Systems and Methods of Use, which are incorporated herein by reference in their entireties.

TECHNICAL FIELD

The present disclosure relates generally to general, podiatric, and orthopaedic surgery related to joint deformities. More specifically, but not exclusively, the present disclosure relates to guides, instruments, devices, systems, and methods for maintaining, correcting and/or resurfacing the bones of a joint.

BACKGROUND OF THE INVENTION

Currently available methods for preparing a joint surface require a large incision to allow for performing an "open" technique to remove cartilage and subchondral bone from a patient. The currently used "open" techniques generally involve use of a saw blade to remove the cartilage and subchondral bone, which prevents the use of a minimally invasive approach for preparing the joint surfaces. In addition, these currently used techniques usually are done without the aid of a guide.

Accordingly, it is an object of the present invention to overcome one or more of the above-described drawbacks and/or disadvantages of the currently used techniques. For example, in view of the deficiencies of the current systems and corresponding surgical techniques, it would be desirable to develop devices, instruments, systems and/or methods that allow for preparing a patient's joint surfaces using a minimally invasive approach.

SUMMARY OF THE INVENTION

The present disclosure is directed towards guides, devices and methods for use in maintaining, correcting and/or resurfacing the bone surfaces of a patient's joint.

In one aspect of the present disclosure provided herein, is a guide system. The guide system includes a cut guide and an alignment guide for engagement with the cut guide.

In another aspect of the present disclosure provided herein, is a cleaning system. The cleaning system including a cutting instrument and a guide for receiving the cutting instrument.

In another aspect of the present disclosure provided herein, is a method for using a guide system. The method includes obtaining the guide system. The guide system includes an alignment guide and a cut guide with a base portion, an extension member extending away from a bottom surface of the base portion, and at least one arm extending away from at least one end of the base portion. The method also includes making an incision to expose a joint having a first bone and a second bone. In addition, the method includes inserting the alignment guide into the joint space. The method further includes coupling the cut guide to the alignment guide. In addition, the method includes inserting at least one wire through at least one hole in the cut guide and into at least one of the first bone and the second bone. Additionally, the method includes checking for alignment of the cut guide and removing the alignment guide from the cut guide. The method further includes inserting a cutting instrument through a slot located in the cut guide to remove at least one portion of the first bone or the second bone. Furthermore, the method includes removing the at least one wire from at least one of the first bone and the second bone and the cut guide. Then, the method includes aligning the joint for fixation.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 7 is an exploded, first end view of the cut guide and the alignment guide of the guide system of FIG. 1, in accordance with an aspect of the present disclosure;

FIG. 8 is an exploded, side view of the cut guide and the alignment guide of the guide system of FIG. 1, in accordance with an aspect of the present disclosure;

FIG. 15 is a first side view of the cut guide of the guide system of FIG. 1, in accordance with an aspect of the present disclosure;

FIG. 16 is a second side view of the cut guide of the guide system of FIG. 1, in accordance with an aspect of the present disclosure;

DETAILED DESCRIPTION FOR CARRYING OUT THE INVENTION

Figure 1:
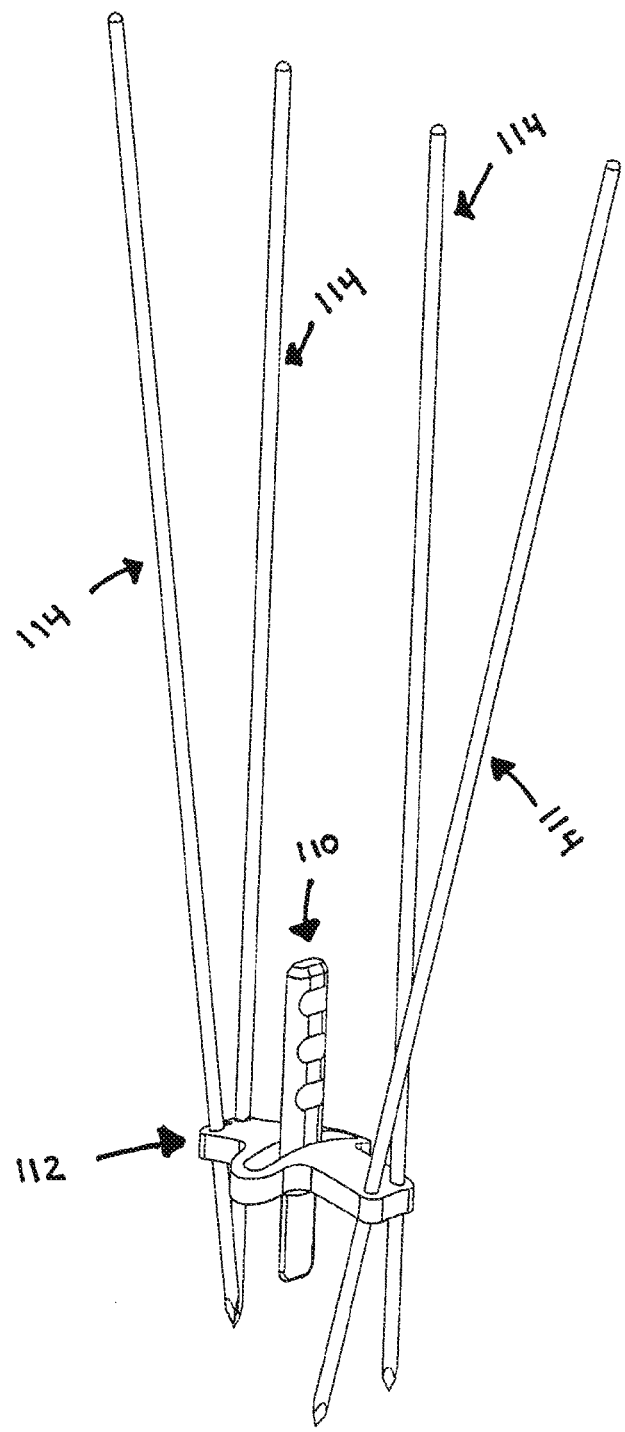
FIG. 1 is a perspective view of one embodiment of a guide system, in accordance with an aspect of the present disclosure.
Figure 2:
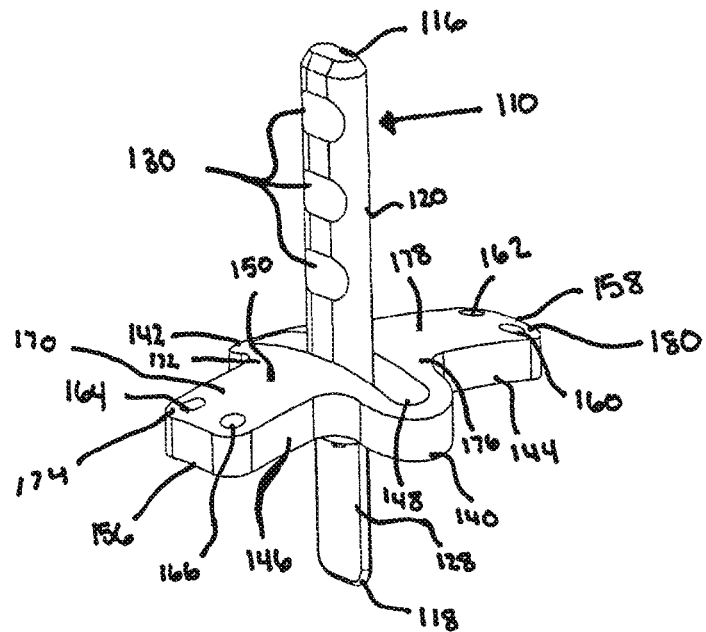
FIG. 2 is a first perspective view of a cut guide and an alignment guide of the guide system of FIG. 1, in accordance with an aspect of the present disclosure.
Figure 3:
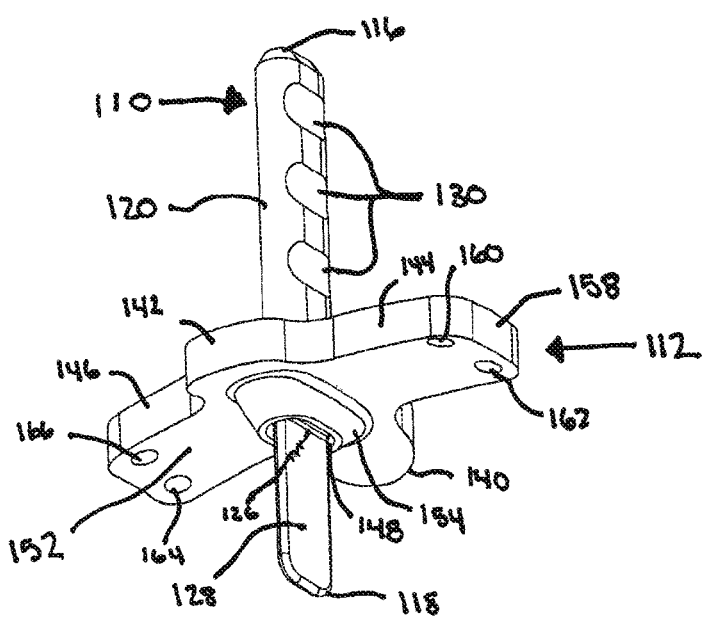
FIG. 3 is a second perspective view of the cut guide and the alignment guide of the guide system of FIG. 1, in accordance with an aspect of the present disclosure.

Generally stated, disclosed herein are guides, instruments, devices, systems, and methods for maintaining and/or correcting a joint using methods for resurfacing the bone surfaces of a joint. Further, methods for using the guides, instruments, devices, systems, and methods for maintaining, resurfacing, and/or correcting a joint are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the foot, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right foot may be mirrored so that they likewise function with the left foot. Further, the devices, systems, instrumentation and methods, and the aspects, components, features and the like thereof, disclosed herein are described with respect to the foot for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-17 there is an illustrated guide system 100. The guide system 100 includes an alignment guide 110, a cut guide 112, and at least one directional attachment member 114, which may be, for example, a guide wire, k-wire, olive wire, or the like wire, fastener, or pin to temporarily hold the cut guide 112 to a patient's bones.

Figure 4:
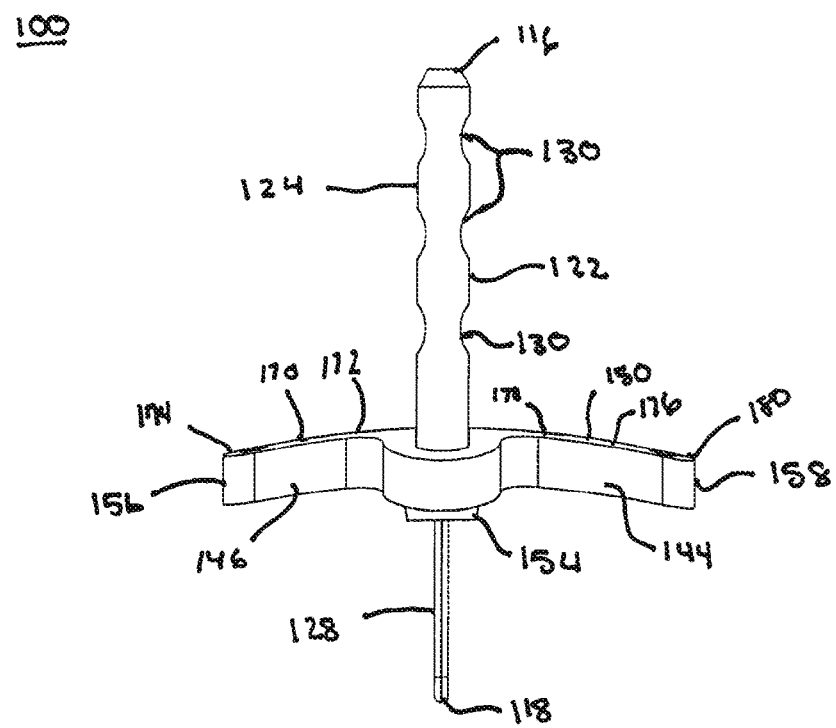
FIG. 4 is a first end view of the cut guide and the alignment guide of the guide system of FIG. 1, in accordance with an aspect of the present disclosure.
Figure 5:
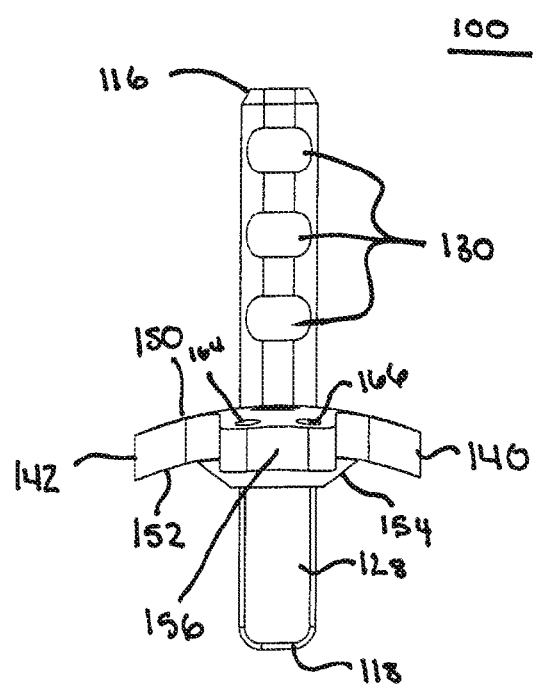
FIG. 5 is a side view of the cut guide and the alignment guide of the guide system of FIG. 1, in accordance with an aspect of the present disclosure.
Figure 6:
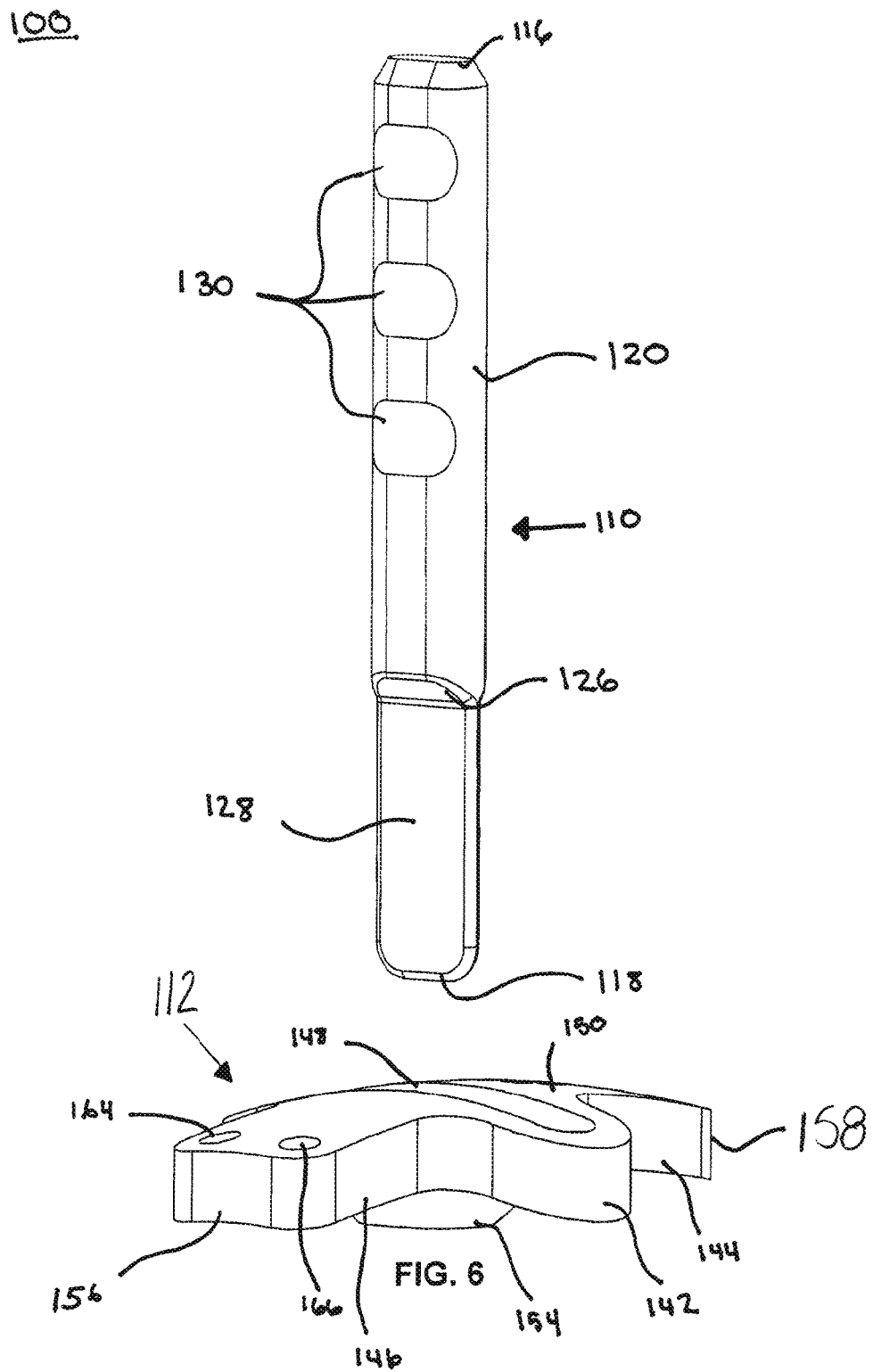
FIG. 6 is an exploded, perspective view of the cut guide and the alignment guide of the guide system of FIG. 1, in accordance with an aspect of the present disclosure.
Figure 9:
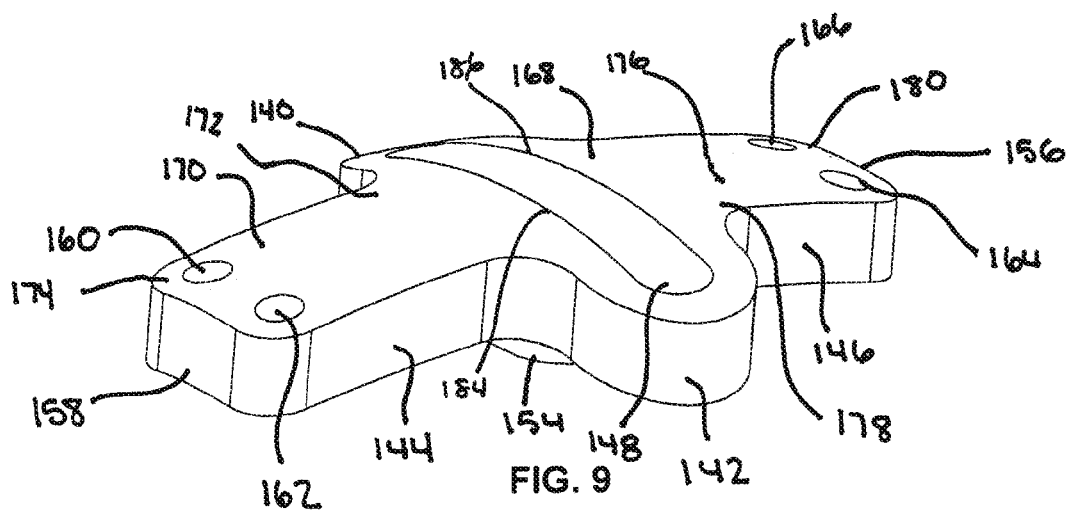
FIG. 9 is a top, perspective view of the cut guide of the guide system of FIG. 1, in accordance with an aspect of the present disclosure.
Figure 10:
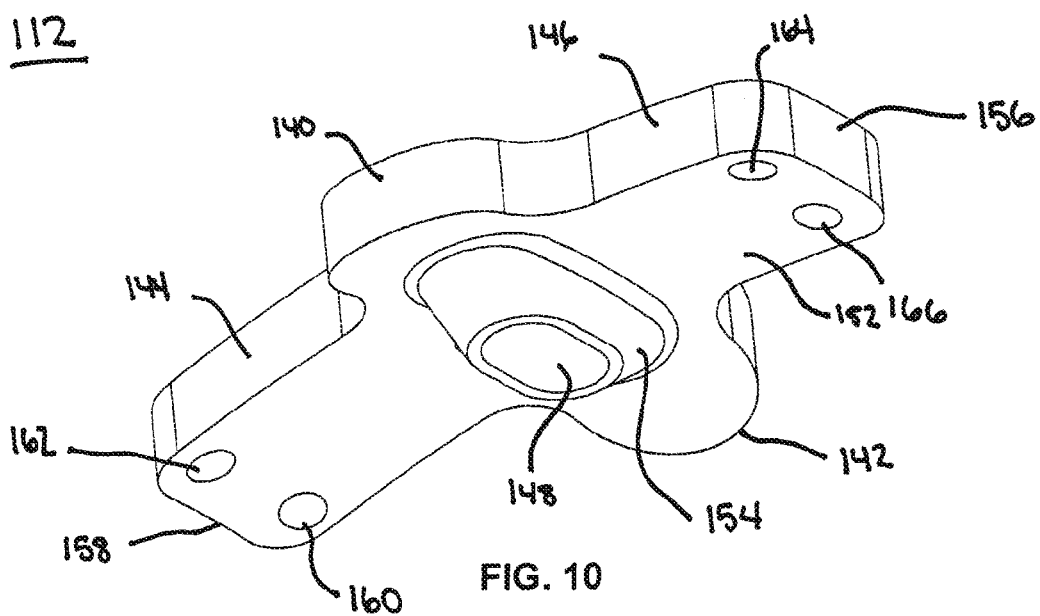
FIG. 10 is a bottom, perspective view of the cut guide of the guide system of FIG. 1, in accordance with an aspect of the present disclosure.

As shown in FIGS. 2-8 the alignment guide 110 includes a first end 116 and a second end 118. The alignment guide 110 also includes a shaft portion 120 and an extension portion 128. The shaft portion 120 extends from the first end 116 toward the second end 118 and engages the extension portion 128 which extends from the second end 118 toward the first end 116. The shaft portion 120 may have, for example, a width larger than the width of the extension portion 128. The shaft portion 120 may be secured to the extension portion 128 by a coupling portion 126. The coupling portion 126 may be tapered as it extends from the shaft portion 120 to the extension portion 128, as shown in FIGS. 6 and 7. The alignment guide 110 also includes a first side 122 opposite a second side 124, as shown in FIGS. 4 and 7. In addition, the shaft portion 120 includes at least one recess 130 positioned on the first side 122 and at least one recess 130 positioned on the second side 124. The recesses 130 may provide, for example, a gripping feature for the user. In an embodiment, the first side 122 includes, for example, three recesses 130 and the second side 124 includes, for example, three recesses 130. Alternative numbers, shapes and sizes of recesses 130 are also contemplated. In further embodiments, the recesses 130 may be removed from the shaft portion 120. The coupling portion 126 may be, for example, tapered on the first side 122 from an exterior surface toward a midline of the alignment guide 110 and tapered on the second side 124 from an exterior surface toward the midline of the alignment guide 110. The taper on the coupling portion 126 may, for example, enable the coupling portion 126 to nestle in the extension member 154 of the alignment guide 110. The extension portion 128 of the alignment guide 110, may be, for example, sized and shaped to allow for full insertion through the alignment guide 112 and into a patient's joint 322, as shown in FIGS. 23-30 and described in greater detail below. In addition, the shaft portion 120 may be, for example, wider than the distal opening of the slot 148 thereby preventing the shaft portion 120 of the alignment guide 110 from extending entirely through the slot 148 and into the joint 322.

With continued reference to FIGS. 2-8 and reference to FIGS. 9-17, the cut guide 112 includes a first side 140 opposite a second side 142, a top surface 150 opposite a bottom surface or bone contacting surface 152, and a first or proximal end 156 opposite a second or distal end 158. The cut guide 112 may be, for example, curved from the first end 156 to the second end 158. The cut guide 112 may also be, for example, curved from the first side 140 to the second side 142 to facilitate placement on the two bones. The cut guide 112 also includes a base portion 168, a first arm 144 extending away from the base portion 168 in a first direction, and a second arm 146 extending away from the base portion in a second direction. The base portion 168 may have, for example, a semi-circular curved outside edge on the first side 140 and a semi-circular curved outside edge on the second side 142.

The first arm 144 may be coupled to the base portion 168 on a first side and the second arm 146 may be coupled to the base portion 168 on a second side, as shown in FIGS. 2-8 and 9-17. The first side may be, for example, opposite the second side. The first arm 144 may include a body portion 170 with a first end 172 and a second end 174. The first end 172 is coupled to the base portion 168 of the cut guide 112 and extends to the distal end 158 of the cut guide 112. The second end 174 of the body portion 168 is positioned at the distal end 158 of the cut guide 112 and may have, for example, rounded or curved edges. The first arm 144 may be, for example, longer than the second arm 146. The first arm 144 may also include at least one hole or opening 160, 162 positioned near the second end 174 of the first arm 144 and extending through the cut guide 112 from the top surface 150 to the bottom surface 152. The at least one hole 160, 162 may be, for example, a first hole 160 and a second hole 162, although alternative numbers of holes are also contemplated to assist with temporarily securing the cut guide 112 to a patient's bones. The first hole 160 may be, for example, spaced apart from the second hole 162 on the second end 180 of the first arm 144. The holes 160, 162 may be positioned, for example, to prevent backing out of the burr guide while in use with a powered instrumentation that may vibrate and cause movement of the instrument. For example, the holes 160, 162 may extend through the cut guide 112 in a converging or diverging orientation to secure the cut guide 112 to the patient's bones.

The second arm 146 may include a body portion 176, with a first end 178 and a second end 180, as shown in FIGS. 2-8 and 9-17. The first end 178 is coupled to the base portion 168 of the cut guide 112 and extends to the proximal end 156 of the cut guide 112. The second end 180 of the body portion 176 is positioned at the proximal end 156 of the cut guide 112 and may have, for example, rounded or curved edges. The second arm 146 may include at least one hole or opening 164, 166 positioned near the second end 180 of the second arm 146 and extending through the cut guide 112 from a top surface 150 to a bottom surface 152. The at least one hole 164, 166 may be, for example, a third hole 164 and a fourth hole 166, although alternative numbers of holes are also contemplated to assist with temporarily securing the cut guide 112 to a patient's bones. The third hole 164 may be, for example, spaced apart from the fourth hole 166 on the second end 180 of the second arm 146. The holes 164, 166 may also be positioned, for example, to prevent backing out of the burr guide while in use with a powered instrumentation that may vibrate and cause movement of the instrument. For example, the holes 164, 166 may extend through the cut guide 112 in a converging or diverging orientation to secure the cut guide 112 to the patient's bones.

Figure 12:
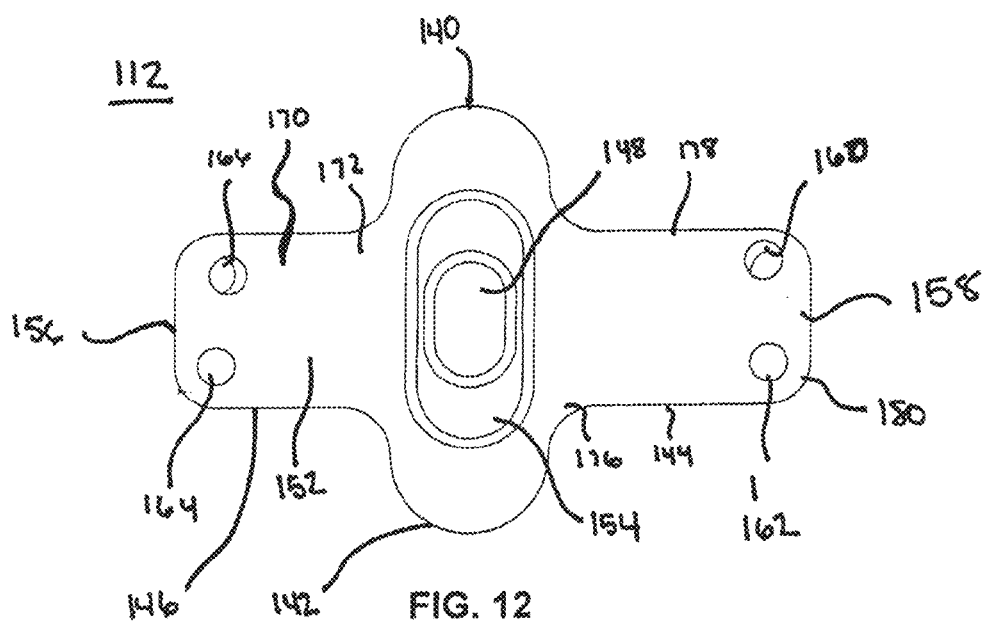
FIG. 12 is a bottom view of the cut guide of the guide system of FIG. 1, in accordance with an aspect of the present disclosure.
Figure 13:
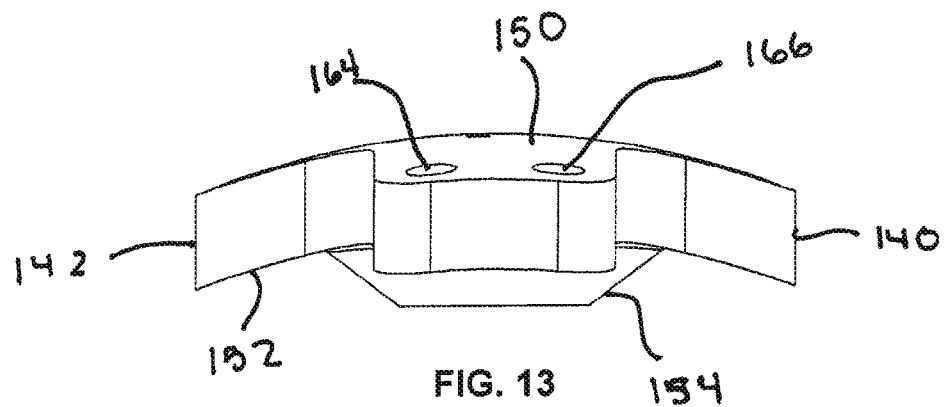
FIG. 13 is a first end view of the cut guide of the guide system of FIG. 1, in accordance with an aspect of the present disclosure.
Figure 14:
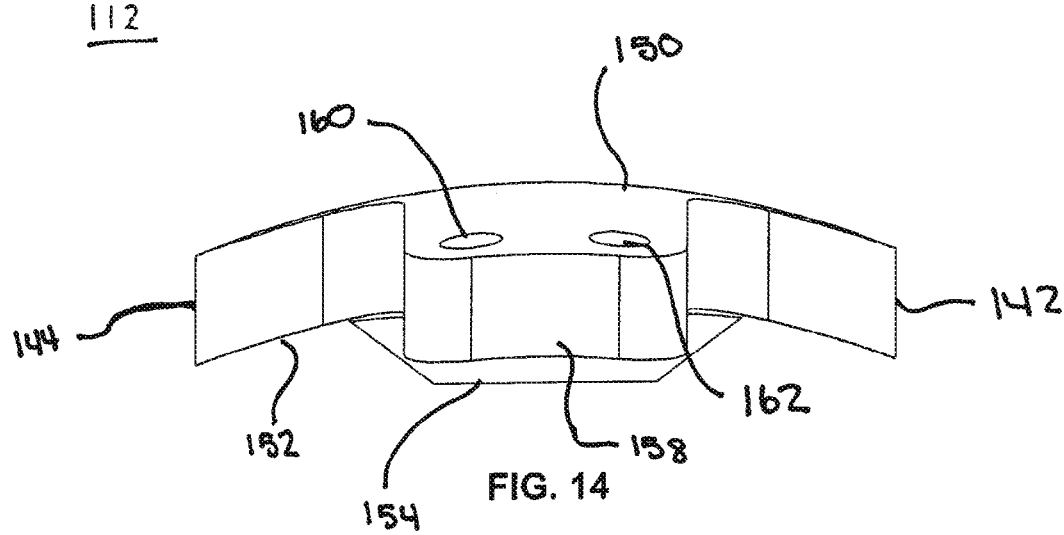
FIG. 14 is a second end view of the cut guide of the guide system of FIG. 1, in accordance with an aspect of the present disclosure.

Referring now to FIGS. 10 and 12-17, the cut guide 112 may further include an extension member 154 extending away from the bottom surface 152 of the base portion 168 of the cut guide 112. The extension member 154 may extend, for example, at least partially between the first side 140 and the second side 142 of the cut guide 112. The extension member 154 may also be, for example, tapered as it extends away from the bottom surface 152 of the cut guide 112, as shown in FIGS. 13 and 14. The extension member 154 may be, for example, tapered in a proximal-distal direction, a dorsal-plantar direction, and medial-lateral direction. In an embodiment, the extension member 154 may be, for example, tapered as it extends away from the bottom surface 152 of the cut guide 112 between the first side 140 and second side 142, as well as between the first end 156 and the second end 158. As illustrated, the extension member 154 may have, for example, a generally conical shape with an elliptical or oval cross section. The openings at the top and bottom of the extension member 154 may also have, for example, an oval or elliptical shape. The extension member 154 may also, for example, taper in a funneling fashion, as it extends away from the bottom surface 152 of the cut guide 112.

Figure 11:
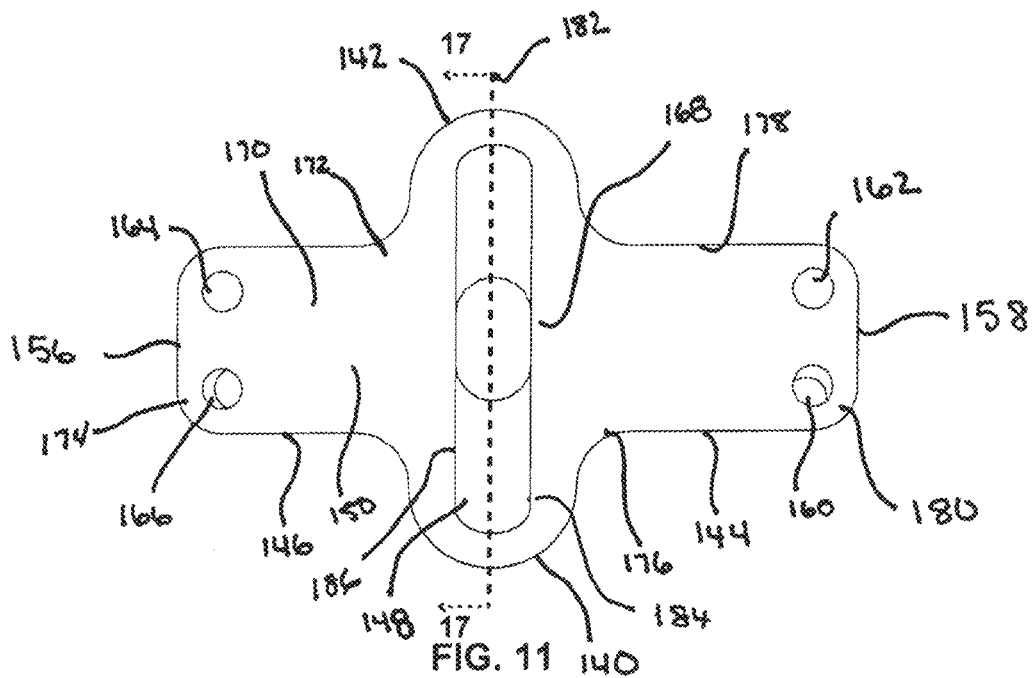
FIG. 11 is a top view of the cut guide of the guide system of FIG. 1, in accordance with an aspect of the present disclosure.
Figure 17:
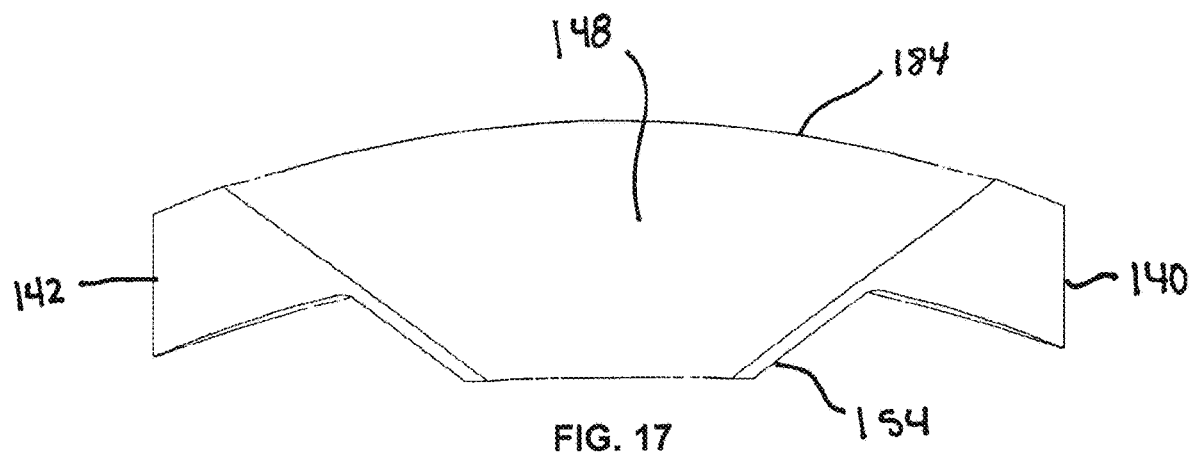
FIG. 17 is a cross-sectional view of the cut guide of the guide system of FIG. 1, taken along line 17-17 in FIG. 11, in accordance with an aspect of the present disclosure.

As shown in FIGS. 2-3, 6-7, 9-12 and 15-17, the cut guide 112 also includes a slot or opening 148. The slot 148 may be, for example, positioned longitudinally between the first arm 144 and second arm 146 and may extend at least partially between the first side 140 and the second side 142. The slot 148 may extend through the cut guide 112 from the top surface 150 to the bottom surface 152 and further through the extension member 154. As shown in FIG. 17, the slot 148 may taper as it extends from the top surface 150 of the cut guide 112 through the cut guide 112 and through the extension member 154. As shown in FIGS. 11 and 12, the opening of the slot 148 at the top surface 150 of the cut guide 112 is larger than the opening of the slot 148 at the bottom surface of the extension member 154. The slot 148 has a first side 184 and a second side 186 extending from the top surface 152 of the cut guide 112 through the base portion 168 and the extending member 154. The top surface of the first side 184 and second side 186 of the slot 148 may extend, for example, parallel to the proximal end 156 and distal end 158 of the cut guide 112. However, alternative orientations of the first side 184 with respect to the second side 186 of the slot 148 are also contemplated.

Referring now to FIGS. 18-22, a cleaning system 200 is illustrated. The cleaning system 200 may include a guide 204 and a cutting instrument 202. The guide or cleaning guide 204 may include a base portion 234 with a first or top surface 228 opposite a second or bottom surface 230, a first end 224 opposite a second end 226, and a first side 240 opposite a second side 242. The top surface 228 is positioned parallel to the bottom surface 230 and the first side 240 is positioned parallel to the second side 242. The first end 224 may be, for example, symmetric to the second end 226. Furthermore, the outside edge of the first end 224 and the outside edge of the second end 226 may be, for example, semicircular in nature or have a semicircular shape. The first or top surface 228 may include a recess 232 positioned near the second end 226 of the guide 204. The recess 232 may be, for example, a circular recess 232 any may be inset into the top surface 228 of the guide 204. The recess 232 may include, for example, an opening 222, extending from the first surface 228 through the base portion 234 to the second surface 228. The opening 222 may be, for example, shaped to guide the cutting instrument 202 into the opening 222 such that material, such as, soft tissue from the burr is removed from the flutes while passing through the opening 222. For example, the opening 222 may be shaped to match the shape of the shape of the cutting portion 220 of the cutting instrument 202. The opening 222 may be, for example, made of a flexible or deformable material to allow for insertion, removal, and rotation of the cutting instrument 202.

Figure 18:
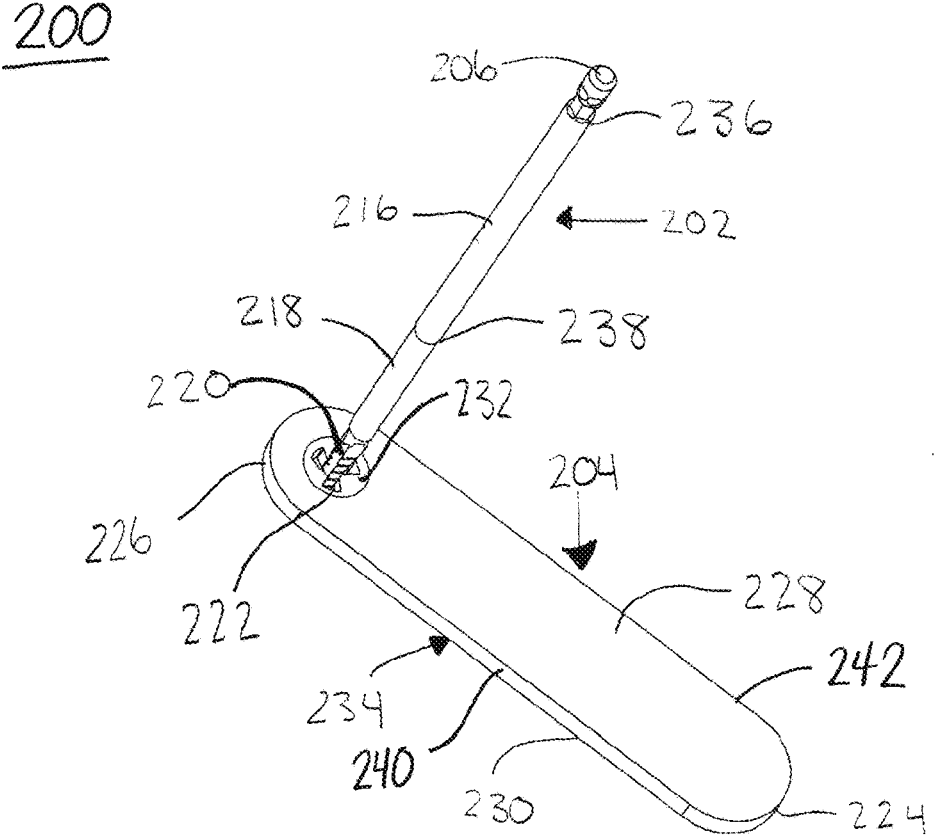
FIG. 18 is a perspective view of a cleaning system, in accordance with an aspect of the present disclosure
Figure 19:
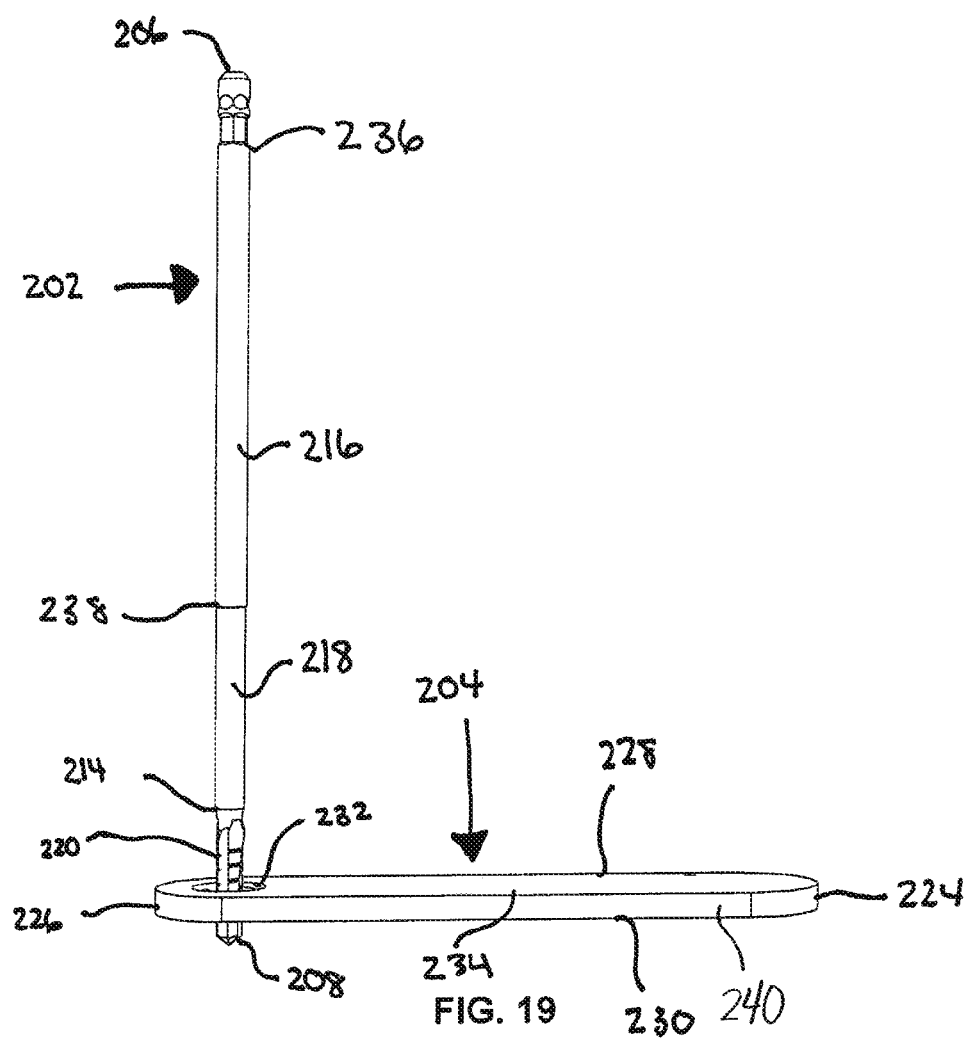
FIG. 19 is a side view of the cleaning system of FIG. 18, in accordance with an aspect of the present disclosure.
Figure 20:
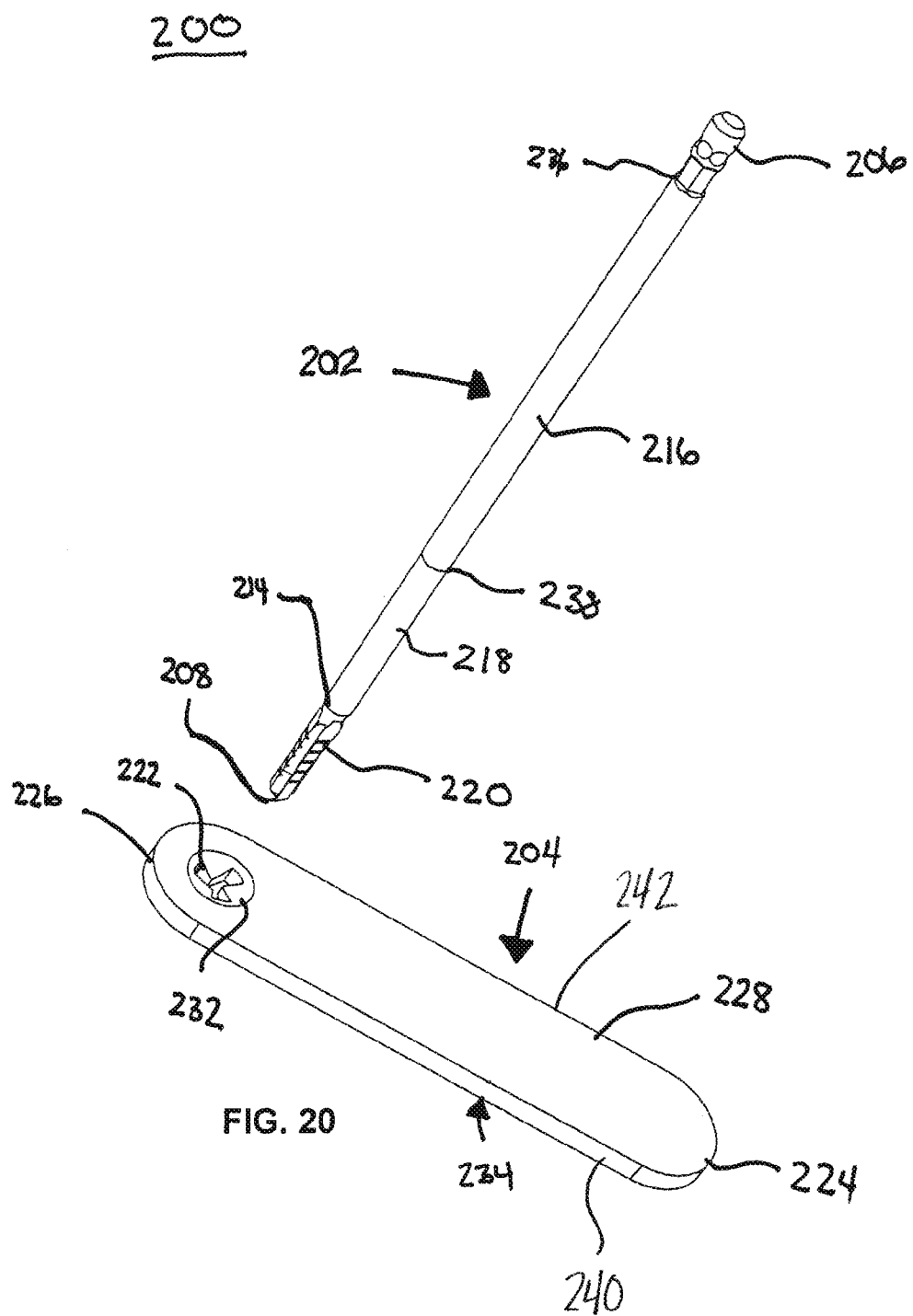
FIG. 20 is an exploded, top, perspective view of the cleaning system of FIG. 18, in accordance with an aspect of the present disclosure.
Figure 21:
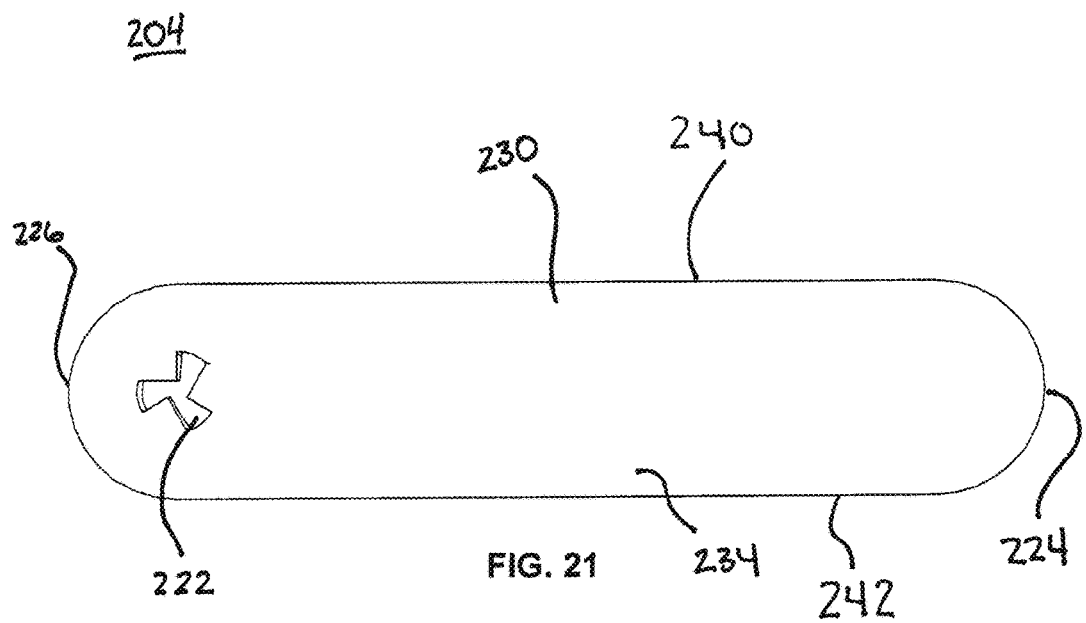
FIG. 21 is a bottom view of the cleaning instrument of FIG. 18, in accordance with an aspect of the present disclosure.
Figure 22:
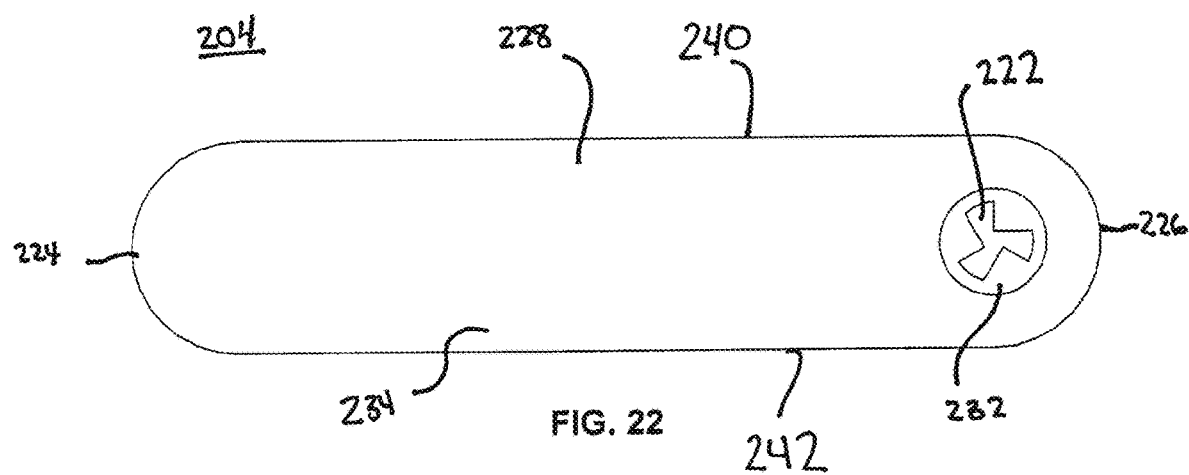
FIG. 22 is a top view of the cleaning instrument of FIG. 18, in accordance with an aspect of the present disclosure.
Figure 23:
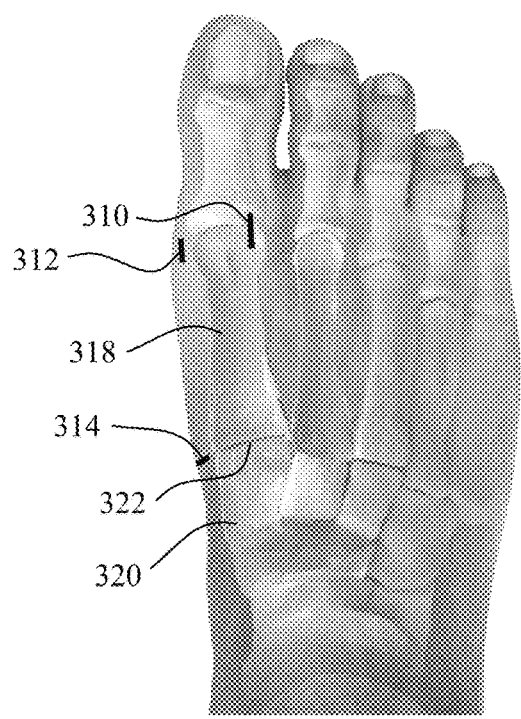
FIG. 23 depicts a dorsal view of a patient's foot showing the incisions of a surgical procedure, in accordance with an aspect of the present disclosure.
Figure 24:
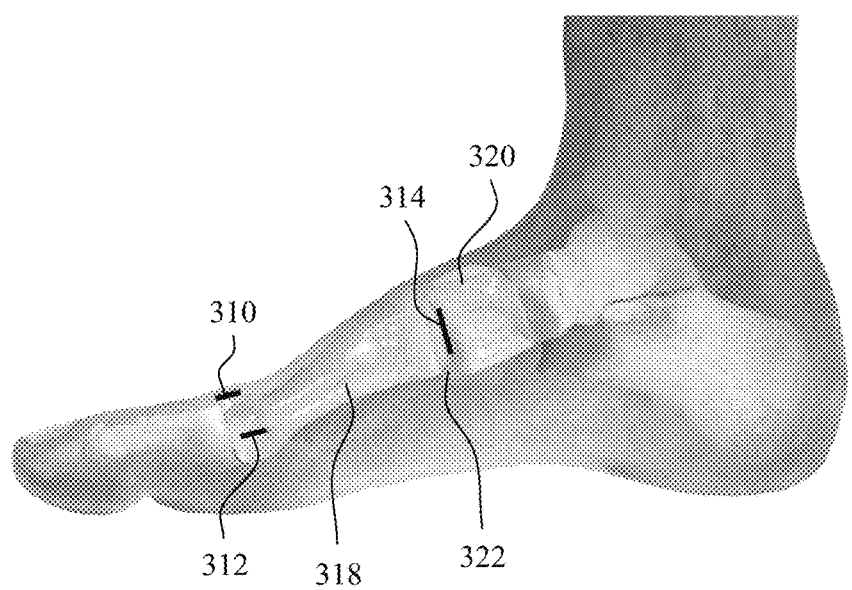
FIG. 24 depicts a medial view of the foot of FIG. 23, in accordance with an aspect of the present disclosure.
Figure 25:
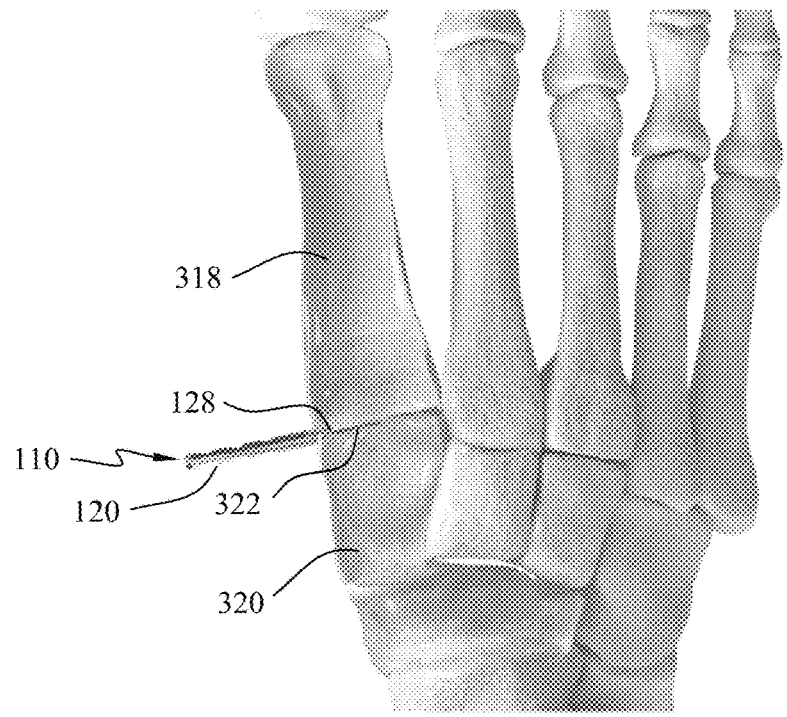
FIG. 25 depicts a dorsal view of the foot of FIG. 23 after inserting the alignment guide of FIG. 1 into a joint, in accordance with an aspect of the present disclosure.
Figure 26:
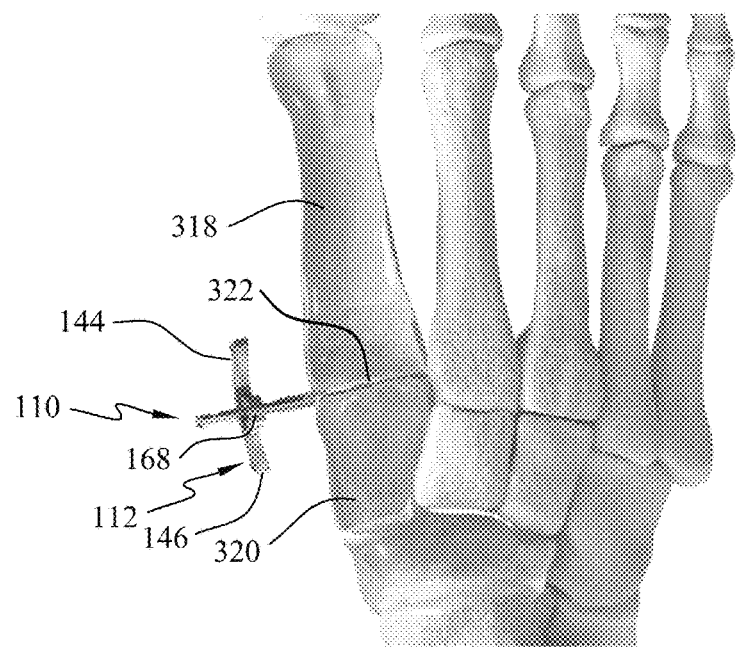
FIG. 26 depicts a dorsal view of the foot and alignment guide of FIG. 25 during insertion of the cut guide of FIG. 1 onto the alignment guide, in accordance with an aspect of the present disclosure.
Figure 27:
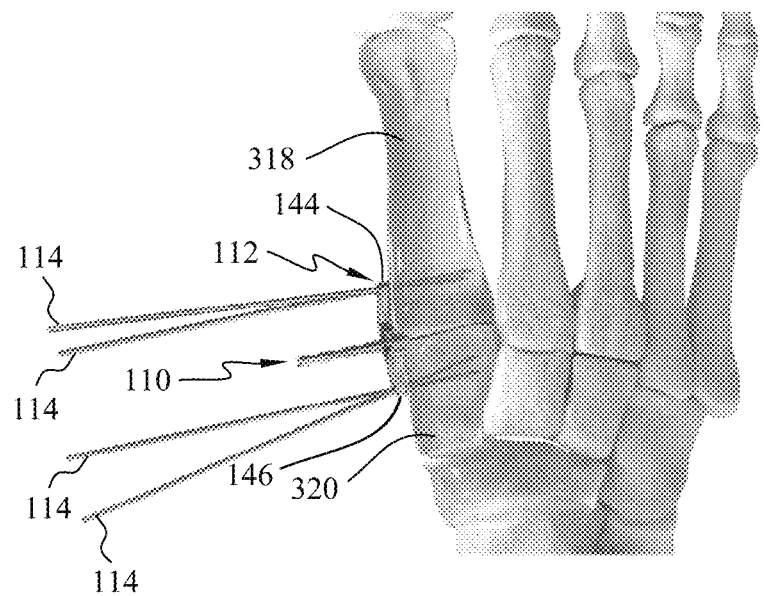
FIG. 27 depicts a dorsal view of the foot of FIG. 26 after the cut guide of FIG. 1 is fully inserted onto the alignment guide and guide wires of the guide system of FIG. 1 are inserted through the cut guide, in accordance with an aspect of the present disclosure.
Figure 28:
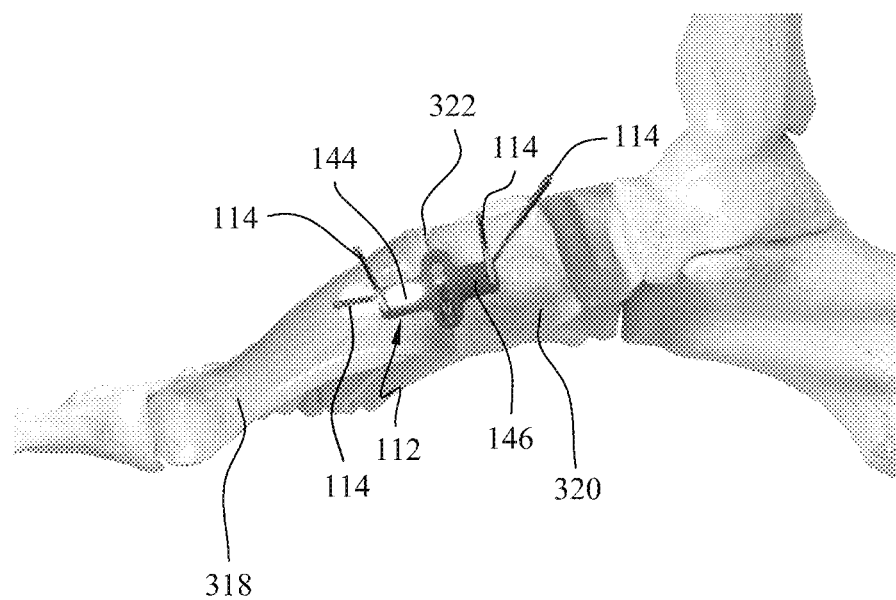
FIG. 28 depicts a medial view of the foot and inserted guide system of FIG. 27, in accordance with an aspect of the present disclosure.
Figure 29:
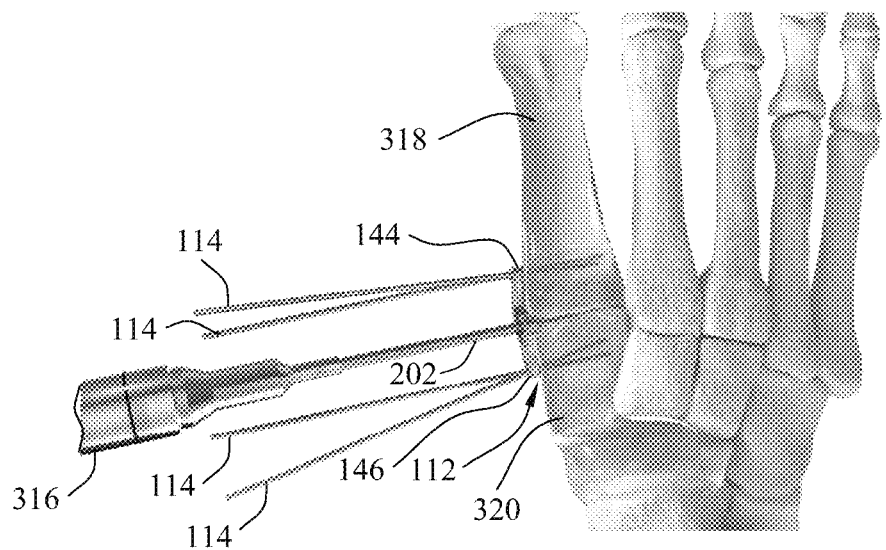
FIG. 29 depicts a dorsal view of the foot of FIG. 28 after removal of the alignment guide and insertion of a burr tool through the cut guide of FIG. 1, in accordance with an aspect of the present disclosure.
Figure 30:
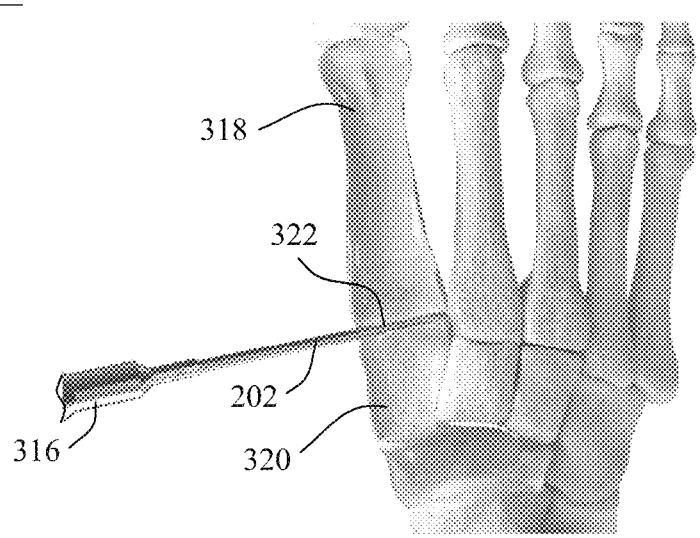
FIG. 30 depicts a dorsal view of the foot of FIG. 29 after removal of the guide system of FIG. 1 and reinsertion of the burr tool of FIG. 29 to complete the bone resurfacing, in accordance with an aspect of the present disclosure.

With continued reference to FIGS. 18 and 19 the cutting instrument 202 includes a first end 206 and a second end 208. The cutting instrument 202 also includes a shaft portion 216 extending from the first end 206 toward the second end 208, a cutting portion 220 extending from the second end 208 toward the first end 206, and a coupling portion 214 extending between the shaft portion 216 and the cutting portion 220. The shaft portion 216 of the cutting instrument 202 also includes a tapered portion 218, which is coupled to, and extends away from, the point 238 of the shaft portion 216 to the coupling portion 214. In addition, the cutting portion 220, may have, for example, at least one cutting flute and the shape of the at least one cutting flute of the cutting portion 220 may match the shape of the opening 222 of the cleaning guide 204. The first end 206 also includes an attachment portion 236 for coupling to a tool 316, as shown in FIGS. 29-30, for powering the cutting instrument 202. Although one type of attachment portion 236 is shown, alternative attachment portions for coupling the cutting instrument 202 to a tool 316, as shown in FIGS. 29-30, for rotating the cutting portion 214 are also contemplated.

Now with reference to FIGS. 23-30, a method 300 for using the guide system 100 is illustrated. The guide system may be, for example, the guide system 100 described in greater detail above with reference to FIGS. 1-17 and which will not be described again here for brevity sake. The method may include, for example, obtaining a guide system 100 and preparing the foot for receiving the guide system 100. Preparing the foot may include making at least one incision, such as incision 314. In the depicted method, preparing the foot includes, for example, making a first incision 310 to release the adductor tendon, a second incision 312 to resect the medial eminence, and a third incision 314 to expose the joint 322 as well as at least a portion of the first bone 318 and the second bone 320 to prepare the joint surfaces. Resecting the medial eminence may be performed, for example, by making the incision through the capsule and inserting the resection instrument, such as a burr, into the capsule. Next, the burr may be started on a low speed before contacting bone and moved into contact with the bone using a sweeping motion to resect the medial eminence until the cut is in-line with the shaft of the metatarsal and the entire medial eminence is removed.

Next, the method 300 may include inserting the alignment guide 110 of the guide system 100 into the joint 322 through the third incision 314 and confirming the placement of the alignment guide 110 using, for example, fluoroscopy. Then, the method 300, may include inserting the cut guide 112 onto the alignment guide 312. The guide 112 may be positioned with the first arm 144 distally orientated and the bottom surface 152 contacting the bones. The method 300 may also include inserting a first wire 114 through the hole 164 located on the first end 156 of the cut guide 112. Then, the method may include inserting a second wire 114 through the hole 162 located on the second end 158 of the cut guide 112. Additionally, the method 300 may include inserting a third wire 114 through the remaining hole 166 on the first end 156, and the remaining hole 160 on the second end 158 of the cut guide 112. Next, the method 300 may include removing the alignment guide 110 from the joint 322.

With continued reference to FIGS. 29-30, the method 300 may include preparing the joint 322. Preparing the joint may include obtaining a tool 316 with a cutting instrument or burr instrument 202 coupled to the tool 316 and inserting the cutting instrument 202 through the slot 148 of the cut guide 112 and into the joint 322. Preparing the joint may also include starting rotation of the cutting instrument 202 before contacting the first bone, for example, the first metatarsal bone, and then sweeping the cutting instrument 202 in a dorsal-plantar motion to remove cartilage and subchondral bone from the joint surface of both bones of the joint 322 and prepare the bone for arthrodesis. Then, the method 300 may include removing the cut guide 112 from the joint 322 and inserting the rotating cutting instrument 202 of the tool 316 into the joint 322 through path created by the alignment guide 112 to complete the joint resection dorsally and plantarly. Although not shown, the method may then include using the guide 204 to remove additional cartilage and/or bone from the cutting instrument 202.

After the above method 300 of preparing the joint is complete, the method may then include inserting an intramedullary nail across the joint 322. In an embodiment, the method of inserting an intramedullary nail may be as described in greater detail in U.S. application Ser. No. 15/907,850 (International Application No. PCT/US2018/020046), which will not be described again here for brevity sake.

As may be recognized by those of ordinary skill in the art based on the teachings herein, numerous changes and modifications may be made to the above-described and other embodiments of the present disclosure without departing from the scope of the disclosure. The components of the guide system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the guide system may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A guide system, comprising:
   a cut guide comprising a first end and a second end, wherein the cut guide is curved from the first end to the second end, the cut guide further comprising:
     a base portion, having a top surface and a bottom surface, wherein the base portion comprises:
       at least one slot positioned between a first side and a second side of the base portion;
     an extension member extending away from the bottom surface of the base portion, wherein the extension member is tapered in at least one of a proximal-distal direction, a medial-lateral direction, and a proximal-distal direction as it extends away from the bottom surface of the base portion; and
     at least one arm extending away from at least one end of the base portion; and
   an alignment guide for engagement with the cut guide, wherein the slot extends from the top surface of the base portion through the bottom surface of the base portion and through the extension member.

2. The guide system of claim 1, wherein the extension member comprises:
   a first end, wherein the first end is coupled to the bottom surface of the base portion; and
   a second end.

3. The guide system of claim 1, wherein the at least one arm comprises:
   a first arm extending away from a first end of the base portion; and
   a second arm extending away from a second end of the base portion.

4. The guide system of claim 3, wherein the first arm comprises:
   a body with a first end and a second end, wherein the first end is coupled to a first end of the base portion; and
   at least one hole positioned near the second end of the first arm.

5. The guide system of claim 4, wherein the at least one hole of the first arm comprises:
   a first hole positioned near the second end of the body; and
   a second hole positioned near the second end of the body, wherein the second hole is spaced apart from the first hole, and wherein the first hole and the second hole are angled with respect to each other and the angle is selected from a converging angle or a diverging angle.

6. The guide system of claim 3, wherein the second arm comprises:
   a body with a first end and a second end, wherein the first end is coupled to a second end of the base portion.

7. The guide system claim 6, wherein the second arm further comprises:
   at least one hole positioned near the second end of the second arm.

8. The guide system of claim 7, wherein the at least one hole of the second arm comprises:
   a third hole positioned near the second end of the body; and
   a fourth hole positioned near the second end of the body, wherein the fourth hole is spaced apart from the third hole, and wherein the third hole and the fourth hole are angled with respect to each other and the angle is selected from a converging angle or a diverging angle.

9. The guide system of claim 1, wherein the alignment guide comprises:
   a shaft portion; and
   an extension portion coupled to and extending away from the shaft portion.

10. The guide system of claim 9, wherein the alignment guide further comprises:
    a coupling portion positioned between the shaft portion and the extension portion, wherein the coupling portion is tapered from the shaft portion to the extension portion.

11. The guide system of claim 10, wherein the shaft portion comprises:
    a first side with at least one recess; and
    a second side with at least one recess.

12. The guide system of claim 1, further comprising:
    a cleaning system, wherein the cleaning system comprises:
      a cutting instrument; and
      a cleaning guide with a first end and a second end.

13. The guide system of claim 12, wherein the cleaning guide comprises:
    a recess inset into a top surface of the cleaning guide; and
    an opening extending through the recess from the top surface to a bottom surface of the cleaning guide.

14. The guide system of claim 12, wherein the cutting instrument is received through an opening of the cleaning guide.

15. The guide system of claim 14, wherein the cutting instrument comprises:
    a shaft having a proximal end and a distal end; and
    a cutting portion coupled to and extending away from the proximal end of the shaft.

16. The guide system of claim 1, further comprises:
at least one wire or pin for engaging the cut guide.

17. The guide system of claim 1, wherein the extension member comprises a generally conical shape with an elliptical or oval-shaped cross-section.

18. A method for using a guide system, comprising:
obtaining a cut guide, wherein the cut guide comprises:
- a base portion with a top surface and a bottom surface;
- an extension member extending away from the bottom surface of the base portion, wherein the extension member is tapered in at least one of a proximal-distal direction, a medial-lateral direction, and a proximal-distal direction as it extends away from the bottom surface of the base portion; and
- at least one arm extending away from at least one end of the base portion;

making an incision to expose a joint with a first bone and a second bone;
inserting an alignment guide into a joint space;
coupling the cut guide to the alignment guide;
inserting at least one wire through at least one hole in the cut guide and into at least one of the first bone and the second bone;
checking the alignment of the cut guide;
removing the alignment guide from the cut guide;
inserting a cutting instrument through a slot in the cut guide to remove at least a portion of the first bone or the second bone;
removing the at least one wire from the at least one of the first bone and the second bone and the cut guide; and
aligning the joint for fixation.

* * * * *